United States Patent [19]

Mees

[11] 4,211,746
[45] Jul. 8, 1980

[54] FLAME IONIZATION DETECTOR

[75] Inventor: Rudolf A. Mees, Nieuwkoop, Netherlands

[73] Assignee: WTI Wetenschappelijk Technische Instrumentatie B.V., 's-Gravenzande, Netherlands

[21] Appl. No.: 890,929

[22] Filed: Mar. 28, 1978

[30] Foreign Application Priority Data

Apr. 1, 1977 [NL] Netherlands ............................ 7703583

[51] Int. Cl.$^2$ ...................... G01N 27/62; G01N 31/12
[52] U.S. Cl. .................................................... 422/54
[58] Field of Search ........ 23/254 E, 254 EF, 253 PC; 48/192; 220/88 R, 88 A; 422/54

[56] References Cited

U.S. PATENT DOCUMENTS

| | | | |
|---|---|---|---|
| 2,821,991 | 2/1958 | Marx | 48/192 X |
| 3,455,657 | 7/1969 | Jentzsch et al. | 23/254 EF |
| 3,542,516 | 11/1970 | Clardy | 23/254 EF X |
| 3,607,084 | 12/1971 | Mackey et al. | 23/232 E |
| 3,711,259 | 1/1973 | Gurney | 48/192 |
| 3,738,810 | 6/1973 | Clinton et al. | 23/230 PC |
| 3,840,343 | 10/1974 | Riedmann et al. | 23/254 EF |
| 4,019,863 | 4/1977 | Jenkins et al. | 23/254 E X |

FOREIGN PATENT DOCUMENTS 1523068  9/1969  Fed. Rep. of Germany ........ 23/254 E Primary Examiner—Arnold Turk
Attorney, Agent, or Firm—Weingarten, Maxham & Schurgin

[57] ABSTRACT

Flame ionization detector in which the burner consists of electrically conductive material, preferably a noble metal, and is one of the electrodes in the apparatus. The mixture of fuel gas and sample is ignited by passing a current through the burner to incandesce the same. The burner is preferably a hairpin-shaped capillary tube with an aperture in the hairpin bend, disposed in the upper part of the detector with the aperture facing the bottom part of the detector. There is also described a flame trap for preventing propagation of flame into discharge line and facilities connected to it. The detector is designed to meet extreme requirements for dependability and reliability, such as when used in apparatus for monitoring anesthesia in patients.

10 Claims, 1 Drawing Figure

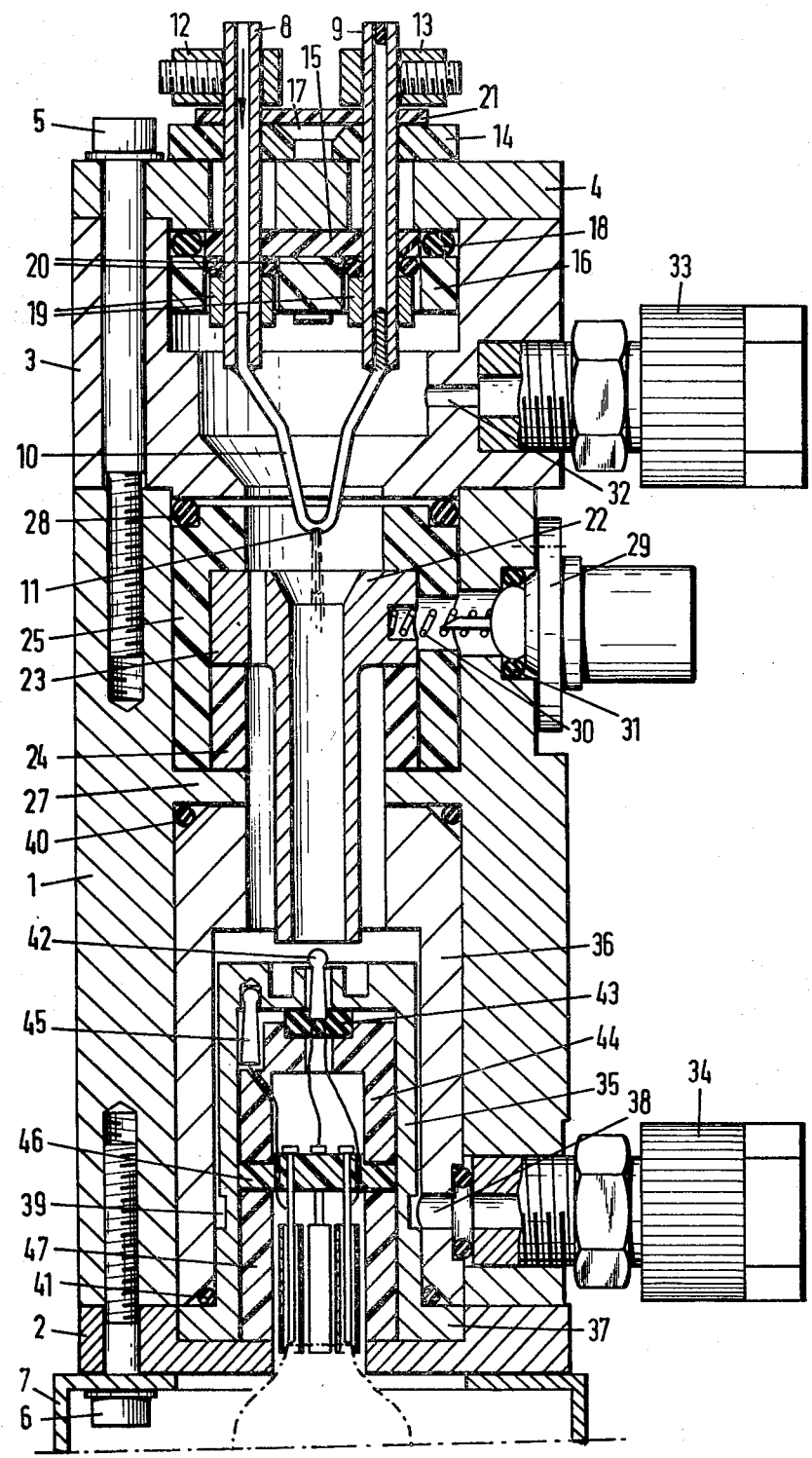

FLAME IONIZATION DETECTOR

This invention relates to a flame ionization detector.

A flame ionization detector commonly comprises a housing, a burner disposed within the housing, a supply line for feeding fuel gas and for feeding materials to be investigated to the burner, means for igniting a flame on the burner, electrodes adjacent to the burner mouth, electrical leads for the electrodes, passing in an electrically insulated manner through the wall of the housing, an air supply conduit, and a discharge conduit for discharging air and waste products.

Such apparatus is generally known and described, for example, in the book entitled Basic Gas Chromatography (Varian Aerograph, 1967). The flame ionization detector described in this book is suitable for use in gas chromatography. Such apparatus is, however, also used in other fields.

In the prior apparatus, the means for igniting a flame on the burner is an incandescent filament (coil) that is disposed at some distance from the burner, and can be connected to the terminals of a battery. When a current is passed from the battery through the filament, the filament incandesces, whereby a combustible gas mixture issuing from the burner mouth is ignited. Owing to the overall construction, this ignition is accompanied by a minor explosion, and it is not always certain that the flame is indeed burning after the explosion. In apparatus required to be highly reliable and simple in operation, this is not desirable. Furthermore, it an amount of combustible gas should happen to accumulate within the apparatus and be ignited, there is the risk that a flame propagates into the discharge conduit, which may lead to damage to apparatus which may be connected to it (e.g. a suction pump). Such problems may perhaps not be objectionable in apparatus for general laboratory use, but for certain uses requiring a very high degree of reliability, for example, because the apparatus is operated by attendants not otherwise skilled in the field of flame ionization detectors, the above effects are undesirable.

It is an object of the present invention to provide a flame ionization detector that is highly reliable and can be used, for example, in apparatus for monitoring anesthesia in a patient. It will be clear that the flame ionization detector used in an anesthesia monitor should be extremely reliable.

This object is realized, according to the invention, in a flame ionization detector in which the burner consists of electrically conductive material and serves as an electrode, whilst the means for igniting a flame on the burner are means for causing a current to flow through the burner to cause the burner to incandesce.

In a preferred embodiment of the present invention, the burner is a hairpin-shaped capillary tube with an aperture in the hairpin bend of the tube, and the apparatus further comprises means for supplying fuel gas and material to be investigated via the capillary tube and causing the same to issue from the tube through the aperture.

In the apparatus according to the invention, the flame is ignited by incandescing the burner mouth, which also serves as an electrode of the detector, by passing a current through it. The fuel gas is then heated to above its ignition temperature, and as soon as it comes into contact with oxygen (e.g., in the air supplied outside the burner mouth), it is ignited. The advantage of such a construction is that it is not necessary for there to be a combustible mixture above the burner before the flame can be ignited, and the occurrence of explosions during the ignition is, therefore, not necessary. Ignition is effected more readily than when a separate incandescent filament is used, and the apparatus is consequently more reliable in operation. Furthermore the ratio of hydrogen (or other fuel gas) to oxygen is less critical than the prior devices, and this ratio can accordingly be better adapted to optimum operating conditions. Commonly the ratio of these gas streams for maximum sensitivity differs from the ratio required for best ignitibility. At optimum sensitivity the stability of the flame is greatest, too. In the apparatus according to the invention that ratio can be used while nevertheless good ignitibility of the flame is ensured.

In the flame ionization detector according to the instant invention, the burner preferably consists of a noble metal, for example, platinum, in order that it may be resistant to any attack from possibly corrosive products of combustion.

In a further preferred embodiment of the invention,, the burner is arranged in the top part of the detector so that the hairpin bend of the burner is the bottom part of the burner with the aperture of the hairpin being present at the side facing the bottom part of the housing.

In this embodiment the flame burns downwards. The advantage is that if the waste products issuing from the flame contain liquids or solids in particulate form, these particles or droplets fall down. In an apparatus in which the burner is in the top portion, the discharge conduit for combustion gases and waste products is disposed below the burner, so that all waste products, including solid particles and droplets, move in the same direction. With such an arrangement it is possible for the measuring electrodes to be insulated at a position (i.e. to be passed to the outside through the wall of the apparatus in an insulated manner) where only clean gases pass the insulation. As a consequence the insulation remains totally free from contamination, so that a long service period is possible without the need for the apparatus to be internally cleaned. In traditional apparatus, however, in which the flame is situated in the bottom part, the waste gases move upwardly and particles and droplets fall down, which causes fouling of the burner proper and its insulation. Furthermore in that case there is a contaminating stream in two directions, which makes it difficult to find a suitable location for insulating the electrodes.

A different embodiment of the apparatus according to this invention comprises a housing, a burner arranged within the housing, a supply line for feeding fuel gas and for feeding materials to be investigated to the burner, means for igniting a flame on the burner, electrodes in the vicinity of the burner mouth, leads for said electrodes, passed through the wall of the housing in an insulated manner, a supply line for air and a discharge line for air and waste products, and means arranged in the space between the place where the burner is disposed and the discharge line for air and waste products for preventing the ignition of possible combustible gases in the discharge line, or the propagation of flames into the discharge line, in particular during the ignition of the flame.

Preferably the means for preventing ignition and/or flames in the discharge line consist of two substantially concentric bushings, the inner one of which is closed at the top, and whose dimensions are such that there is a narrow gap between the outer wall surface of the inner bushing and the inner wall surface of the outer bushing, through which gap the gases to be discharged have to move before reaching the discharge line, and in which these gases are at the same time sufficiently cooled.

Such a flame trap is of particular importance if the flame ionization detector is operated at a reduced pressure, as is the case in an anesthesia monitor. A conventional detector often has a discharge line in open communication with the ambient atmosphere, so that the occurrence of combustion in the discharge line is not too objectionable. If the device is operated at a reduced pressure, however, the discharge line is connected to pump means, and flashing in the discharge line is certainly undesirable. The above-described flame trap, or flash arrester, prevents this effect.

In one embodiment of the apparatus according to the invention with a flame trap, the latter is in the space where the flame burns and where, consequently, hot gases are present, such as waste products. Such hot gases may be very corrosive, so that proper materials should be selected for the parts of the flame trap. This is all the more important as a very narrow gap, preferably of the order of 0.1 mm, is used in the flame trap, which gap is liable to become clogged in the event of corrosive effects. For that reason the parts of the flame trap preferably consist of press-moulded aluminum oxide, ceramics, glass or Teflon (a registered trademark for polytetrafluoroethylene).

The flame trap according to this invention can be used in both detectors with a hairpin burner and detectors with different types of burner. The use in the former has the advantage, however, of resulting in an extremely dependable, sensitive apparatus reliable in operation.

The apparatus according to the present invention is operated in a manner well-known to those skilled in the art. Briefly, this operation comprises igniting the flame on the burner by conducting an incandescing current through the burner. The fuel for the burner is, e.g., hydrogen gas. The sample to be investigated is also supplied through the conduit for supplying the hydrogen gas, and is hence also combusted in the flame. During this process ions are formed, which move to the electrodes. The burner proper is one electrode and is connected to one pole of a battery or other source of voltage (e.g., the positive pole). The other pole of the battery is earth-connected. The other electrode in the flame ionization detector is earth-connected through a resistor. The intensity of the ion current is now measured, for example, as the voltage drop across the resistor. The intensity of the ion current is an indication of the nature and/or amount of the materials combusted in the flame.

The invention will now be described in more detail with reference to the accompanying drawing, in which the single figure illustrates, by way of example, a preferred embodiment of the flame ionization detector according to the present invention in cross-sectional elevation.

The apparatus shown in the drawing comprises a generally cylindrical bottom housing 1, secured at the bottom to a bottom flange 2. Secured to bottom housing 1 is a top housing 3, also of generally cylindrical configuration, and sealed at the top with a top flange 4. Top flange 4, top housing 3 and bottom housing 1 are secured together, for example, by means of bolts, one of which is shown at 5, which bolts are inserted through holes in top flange 4 and top housing 3, and are screwed in internally threaded blind holes in bottom housing 1. In a similar way, bottom flange 2 is secured to bottom housing 1 with bolts 6. Bolts 6 can also serve to secure the unit to a base 7. Bottom flange 2, top flange 4, bottom housing 1 and top housing 3 consist of a suitable metal, such as brass, or stainless steel.

Formed in top flange 4 are a pair of round apertures through which project two hollow connector tubes 8 and 9 for a burner. Tubes 8 and 9 consist of a suitable material capable of conducting electric current, e.g., brass or copper. A burner 10 is secured in the ends of tubes 8 and 9 in the interior of housing 3. Burner 10 is a hairpin-shaped hollow tube of a noble metal, e.g., platinum, with an aperture 11 in the bend of the hairpin at the side facing the bottom of the apparatus. A terminal 12 is secured to tube 8 and a terminal 13 to tube 9. Via terminals 12 and 13 an incandescing current can be applied to hairpin burner 10, by means of which fuel supplied through tube 8 is ignited in aperture 11, so that a downwardly directed flame is burning there.

Tubes 8 and 9 have an outside diameter less than the diameter of the apertures in flange 4 through which they extend into the housing, and in order to keep them electrically insulated from flange 4 and housing 3, insulating disks or rings, closely fitting around the tubes, are provided in contact with the outer and inner surfaces of flange 4. Insulating ring 14, located on the outside, and disks 15 and 16, located on the inside, are maintained in position with a screw 17. In order to prevent any passage of air through the apertures in flange 4 to the inside, or of gases from the interior of the apparatus to the outside, an O-ring 18 is provided around disk 15, which ring is held in position under pressure by disk 16. Tubes 8 and 9 are further fixed in position by fixing sleeves 19 provided around tubes 8 and 9 in the apertures in disk 16, which sleeves also serve for fixing hairpin burner 10 in the ends of tubes 8 and 9. Sleeves 19 press against O-rings 20 for further sealing of the assembly. A further insulating cover ring 21 overlies screw 17 and ring 14.

A highly suitable material for the insulating rings and disks is synthetic resin material, e.g., Teflon and nylon. Sleeves 19 may suitably be formed of brass or stainless steel. Instead of O-rings other types of sealing rings may be used at the places indicated.

In order that all the fuel supplied through tube 8 may be combusted at aperture 11 formed in burner 10, the end of burner 10 inserted in tube 9 has been sealed with solder. The end projecting from the apparatus tube 9 is also sealed with solder.

Hairpin burner 10 also serves as an electrode of the flame ionization detector. Via terminal 12 the desired polarization voltage can be applied to this electrode. Disposed opposite to, and geometrically vertically under, burner 10, is a counter-electrode 22. Electrode 22, consisting e.g. of goldplated stainless steel, has the form of a tube provided at the end proximal to the burner with a laterally outwardly extending collar 23, with which the tubular electrode rests on an insulating ring 24, e.g. of Teflon. Ring 24 and collar 23 have virtually flush outer surfaces, which are in contact with the inner wall of another insulating ring or bushing 25, which is further provided with an internal collar in contact with the end face of electrode 22, so that, as it were, the counter electrode hangs in, and is clamped in, the pack of insulating rings 24 and 25. Rings 24 and 25 themselves rest on a collar 27 extending from the inner wall of bottom housing 1. The rings are held down against collar 27 by the bottom surface of top housing 3, with an O-ring 28, placed between housing 3 and ring 25 on a rebated portion of ring 25, providing for the necessary sealing.

Mounted in the sidewall of bottom housing 1 is a connector 29 for a co-axial cable. If desired, a different connector can be applied. Via the cable to be coupled to connector 29, the signal collected at counter electrode 22 is fed out. Interposed between electrode 22 and connector 29 is a contact spring 30, consisting, e.g., of gold-plated metal, and passed through holes in ring 25 and the sidewall of bottom housing 1. An O-ring provides for the necessary sealing.

For the supply of air to the apparatus, there is provided a passage 32 in the sidewall of top housing 3, to which passage a coupling member 33 is connected, to which a supply conduit for the supply of air can be coupled. For the discharge of air and combustion gases from the apparatus, there is provided a passage through, and a coupling member 34 on, the sidewall of bottom housing 1. Disposed between the counter electrode 22 and the air outlet in the sidewall of bottom housing 1 is a flame trap. Such a device is extremely useful, as any combustible mixtures present in the air to be discharged may be ignited. If the apparatus is operated at a reduced pressure owing to a pump being connected to the air outlet, preventing such ignition is certainly of importance, as otherwise a flame may propagate through the discharge line into the pump system. This purpose is served by the flame trap, which in the instant apparatus consists in essence of two concentric bushings or tubes 35 and 36 of a suitable material, e.g. aluminum oxide, ceramic material, glass or Teflon, which tubes are arranged with a narrow gap (of 0.1 mm, for example) between them, through which gap the gases to be discharged can reach outlet 34. If a flame is formed in the space above the flame trap, i.e., in the space in or below electrode 22, through combustion of a combustible gas mixture, then, even if the combustible gas mixture is also present between tubes 35 and 36 and in the discharge line connected to coupling member 34, the flame cannot exist in the gap between tubes 35 and 36, so that no flame and no ignition can occur in the direction of the pump system. The part concerned may be variously referred to as a flame trap and a flash resistor.

The inner tube 35 of the flame trap is provided at the bottom with a seat 37 resting in a recessed portion of bottom flange 2. Seated on seat 37 is the outer tube 36 of the flame trap, which at the level of coupling member 34 is provided with a passage 38. At the level of passage 38 a peripheral groove 39 is formed in inner tube 35, while the outer diameter of tube 35 above groove 39 is slightly less than the outer diameter below groove 39. Whereas tubes 35 and 36 are virtually in contact with each other below groove 39, there is an extremely narrow gap between them above the groove, through which gap redundant gases can be discharged from the space in the vicinity of the counter electrode to groove 39 and thence through passage 38.

The outer tube 36 of the flame trap has its end surface exactly in contact with the bottom surface of collar 27, and is slightly bevelled at the top outside rim to accommodate a sealing O-ring 40. Likewise tube 36 is slightly bevelled at the bottom inside rim to accommodate a sealing O-ring 41.

The inner tube 35 of the flame trap is closed at the top, save for a central aperture, through which extends a thermistor 42. Thermistor 42 rests at its bottom in a sealing block 43 of, e.g., silicone rubber, through which block the leads for thermistor 42 are passed. Block 43 is supported by a sleeve 44, closed at the top, and provided with passages for the leads of thermistor 42 and of a thermistor 45, the latter thermistor being arranged in a recess of sleeve 44 and extending into a blind bore at the inner and bottom surface of the closure at the top of inner tube 35. Thermistors 42 and 45, which if desired may be thermocouples, serve for monitoring the flame in the apparatus.

Sleeve 44 rests on a disk 46, provided with passages or connectors for the leads of thermistors 42 and 45. Disk 46 rests on a bushing 47, which in turn is supported on bottom flange 2. Via a central aperture in bottom flange 2, the leads for thermistors 42 and 45 for flame-monitoring pass to the outside. Parts 44, 46 and 47 consist of a suitable material, e.g., Teflon or nylon.

It will be clear that the invention is not limited to the embodiment described and shown in the accompanying drawing. Many modifications and alterations will readily occur to those skilled in the art without departing from the scope of the invention.

I claim:

1. A flame ionization detector comprising:
   a housing having an upper portion and a lower portion;
   an electrically-conductive burner disposed within the housing and having a hairpin-shaped bend formed therein;
   a first electrode, the first electrode comprising the electrically-conductive burner;
   an aperture disposed in the hairpin-shaped bend of the burner;
   means for supplying fuel gas and for feeding materials to be investigated to the burner and for causing the fuel gas and the materials to issue from the aperture;
   a second electrode adjacent the aperture;
   a lead electrically connected to the second electrode and passing in an electrically-insulated manner through a wall of the housing to provide access external to the housing of a signal collected at the second electrode;
   an air supply conduit to supply air to the burner;
   a discharge conduit coupled to the housing for discharging air and waste products therefrom;
   means adapted for providing a flow of current through the burner to cause the burner to incandesce and to ignite the fuel gas to provide a flame on the burner; and
   means adapted for applying a voltage differential between the first electrode and the second electrode.

2. A flame ionization detector according to claim 1, wherein the burner is disposed in the upper portion of the housing, wherein hairpin-shaped bend is formed in a section of the burner extending downwardly away from the upper portion and toward the lower portion of the housing, and wherein the aperture faces the lower portion of the housing.

3. A flame ionization detector according to claim 1, wherein the burner is composed of a noble metal.

4. A flame ionization detector according to any one of claims 1, 3, or 2, further comprising a flame trap disposed adjacent to a mouth of the discharge conduit for the discharge of air and waste products.

5. A flame ionization detector comprising:
   a housing;

a burner disposed within the housing;

an aperture disposed in the burner;

means for supplying fuel gas and for feeding materials to be investigated to the burner and for causing the fuel gas and the materials to issue from the aperture;

means for igniting a flame at the aperture;

a pair of spaced electrodes disposed adjacent the aperture and having a voltage differential therebetween;

means for making electrical connection to each of the pair of electrodes;

an air supply conduit to supply air to the burner;

a discharge conduit coupled to the housing for discharging air and waste products therefrom; and a flame trap disposed between the burner and the discharge conduit and adapted to prevent the ignition of combustible gases in the discharge conduit and to prevent propagation of flames into the discharge conduit, the flame trap comprising:

a first substantially cylindrical bushing having a closed upper end facing the burner and a lateral outer wall; and a second bushing disposed substantially concentrically with respect to the first bushing and having a lateral inner wall spaced from and confronting the outer wall of the first bushing, the first bushing outer wall and the second bushing inner wall defining an annular gap therebetween, the gap being adapted to receive the combustible gases prior to their entry into the discharge conduit, and to cool the combustible gases sufficiently to prevent combustion thereof.

6. A flame ionization detector according to claim 5, wherein the flame trap further comprises:

a bore passing through the inner wall of the second bushing and communicating with the discharge conduit and with the gap;

a peripheral groove formed in the outer wall of the first bushing and extending around a circumference thereof, the groove being disposed directly opposite the bore and being in communication with the bore and with the gap; and means sealingly engaging the inner wall of the second bushing to the outer wall of the first bushing between the groove and an end of the first bushing disposed opposite the upper end, whereby the combustible gases entering the gap are prevented from passing beyond the groove but are permitted to pass through the bore and into the discharge conduit.

7. A flame ionization detector according to claim 5 or 6, wherein the gap has a width of the order of 0.1 mm.

8. A flame ionization detector according to claim 7, wherein the first and second bushings are composed of materials selected from the group consisting of aluminum oxide, glass, ceramic material and polytetrafluoroethylene.

9. A flame ionization detector according to claim 5 or 6, wherein the first and second bushings are composed of materials selected from the group consisting of aluminum oxide, glass, ceramic material and polytetrafluoroethylene.

10. A flame ionization detector comprising:

a housing having an upper portion and a lower portion;

an electrically-conductive burner disposed within the housing and having a hairpin-shaped bend formed therein;

a first electrode, the first electrode comprising the electrically-conductive burner;

an aperture disposed in the hairpin-shaped bend of the burner;

means for supplying fuel gas and for feeding materials to be investigated to the burner and for causing the fuel gas and the materials to issue from the aperture;

a second electrode adjacent the aperture;

a lead electrically connected to the second electrode and passing in an electrically-insulated manner through a wall of the housing to provide access external to the housing of a signal collected at the second electrode;

an air supply conduit to supply air to the burner;

a discharge conduit coupled to the housing for discharging air and waste products therefrom;

means adapted for providing a flow of current through the burner to cause the burner to incandesce and to ignite the fuel gas to provide a flame on the burner;

means adapted for applying a voltage differential between the first electrode and the second electrode; and a flame trap disposed between the burner and the discharge conduit and adapted to prevent the ignition of combustible gases in the discharge conduit and to prevent propagation of flames into the discharge conduit, the flame trap comprisinfg:

a first substantially cylindrical bushing having a closed upper end facing the upper portion of the housing and a lateral outer wall;

a second bushing disposed substantially concentrically with respect to the first bushing and having a lateral inner wall spaced from and confronting the outer wall of the first bushing, the inner wall of the second bushing and the outer wall of the first bushing defining an annular gap therebetween, the gap being adapted to receive the combustible gases before entry thereof into the discharge conduit, and to cool the combustible gases sufficiently to prevent combustion thereof;

a bore passing through the inner wall of the second bushing and communicating with the discharge conduit and with the gap;

a peripheral groove formed in the outer wall of the first bushing and extending around a circumference thereof, the groove being disposed directly opposite the bore and being in communication with the bore and with the gap; and means sealingly engaging the inner wall of the second bushing to the outer wall of the first bushing adjacent an edge of the groove facing the lower portion of the housing, the engaging means preventing combustible gases entering the gap from passing beyond the groove while permitting the combustible gases to pass through the bore into the discharge conduit.

* * * * *